US012773158B2

(12) United States Patent
Sugi et al.

(10) Patent No.: US 12,773,158 B2
(45) Date of Patent: Oct. 27, 2026

(54) MUSCULAR RELAXATION MONITORING DEVICE

(71) Applicants: FUKUOKA UNIVERSITY, Fukuoka (JP); Medical Strings Co., Ltd., Fukuoka (JP)

(72) Inventors: Yasuyuki Sugi, Fukuoka (JP); Yukito Kawakami, Fukuoka (JP); Makoto Taroumaru, Fukuoka (JP)

(73) Assignees: FUKUOKA UNIVSERITY, Fukuoka (JP); MEDICAL STRINGS CO., LTD., Kasuga (JP)

( * ) Notice: Subject to any disclaimer, the term of this patent is extended or adjusted under 35 U.S.C. 154(b) by 413 days.

(21) Appl. No.: 18/285,145

(22) PCT Filed: Mar. 24, 2022

(86) PCT No.: PCT/JP2022/014069
§ 371 (c)(1),
(2) Date: Sep. 29, 2023

(87) PCT Pub. No.: WO2022/215546
PCT Pub. Date: Oct. 13, 2022

(65) Prior Publication Data

US 2024/0180476 A1 Jun. 6, 2024

(30) Foreign Application Priority Data

Apr. 6, 2021 (JP) ................................ 2021-064510

(51) Int. Cl.
*A61B 5/395* (2021.01)
*A61B 5/00* (2006.01)
*A61N 1/36* (2006.01)

(52) U.S. Cl.
CPC ............. *A61B 5/395* (2021.01); *A61B 5/746* (2013.01); *A61N 1/36031* (2017.08); *A61B 2562/0219* (2013.01)

(58) Field of Classification Search
CPC . A61B 5/395; A61B 5/746; A61B 2562/0219; A61B 5/11; A61B 5/389; A61N 1/36031
See application file for complete search history.

(56) References Cited

U.S. PATENT DOCUMENTS 4,291,705 A * 9/1981 Severinghaus ........ A61B 5/395 600/554
2004/0243017 A1* 12/2004 Causevic .............. A61B 5/372 600/544

(Continued)

FOREIGN PATENT DOCUMENTS

JP 10-57320 3/1998
JP 2000-342690 12/2000

(Continued)

OTHER PUBLICATIONS

International Search Report dated May 24, 2022 in International Patent Application No. PCT/JP2022/014069.

*Primary Examiner* — Adam J Eiseman
*Assistant Examiner* — Lucy Eppert
(74) *Attorney, Agent, or Firm* — STAAS & HALSEY LLP

(57) ABSTRACT

A muscle relaxation monitoring device monitors the state of muscle relaxation without placing an excessive burden on the patient. The muscle relaxation monitoring device has a current stimulator to supply a stimulating current to muscles of a patient, a reaction detector to detect a stimulus response of the muscle stimulated by the current stimulator. The stimulating current supplied to the muscles of the patient before the application of the muscle relaxant and the stimulating response corresponding to the stimulating current (Continued)

value are recorded in a memory, and when the stimulating response is saturated, the stimulating current value immediately before saturation is used as the optimum current value to be supplied to the patient after administration of the muscle relaxant.

14 Claims, 7 Drawing Sheets

(56) References Cited

U.S. PATENT DOCUMENTS

| | | | | |
|---|---|---|---|---|
| 2012/0245482 | A1 | 9/2012 | Bolser et al. | |
| 2013/0267791 | A1* | 10/2013 | Halperin | A61B 5/6891 600/300 |
| 2018/0035898 | A1* | 2/2018 | Gunderson | A61B 5/287 |
| 2019/0223764 | A1* | 7/2019 | Hulvershorn | A61B 5/24 |
| 2021/0076982 | A1 | 3/2021 | Sarkela et al. | |

FOREIGN PATENT DOCUMENTS

| | | |
|---|---|---|
| JP | 2015-66401 | 4/2015 |
| JP | 2017-113085 | 6/2017 |
| JP | 2019-530528 | 10/2019 |
| JP | 7497792 | 6/2024 |
| WO | WO 2018/071860 A2 | 4/2018 |

* cited by examiner

[Figure 1]
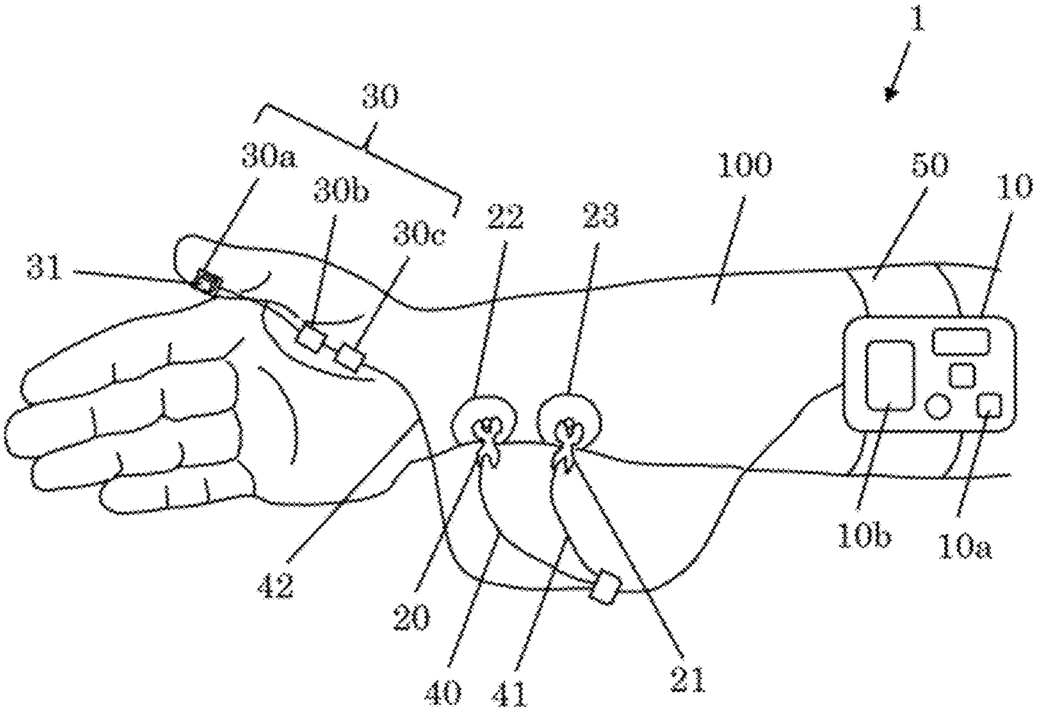

[Figure 2]
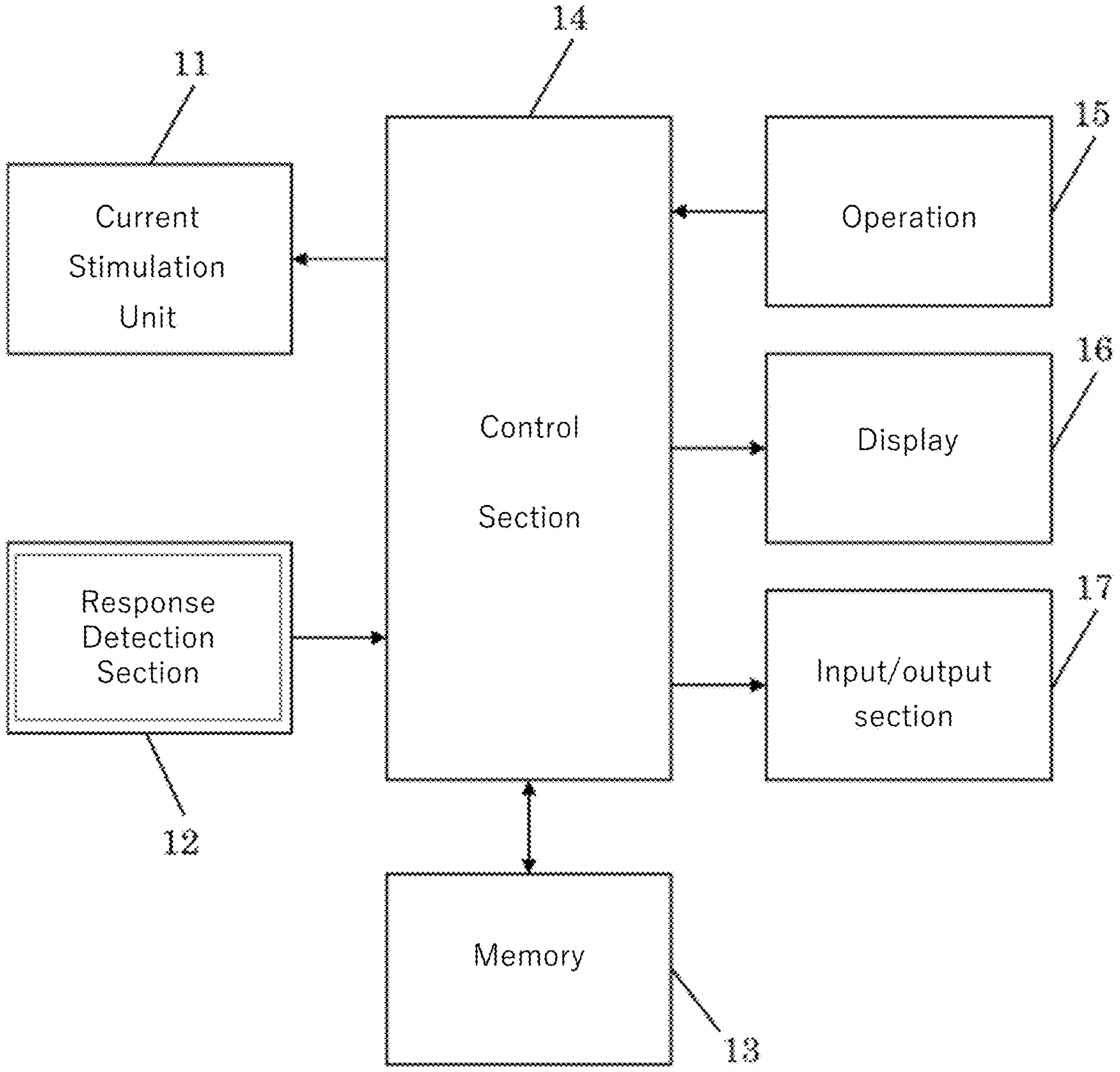

[Figure 3]
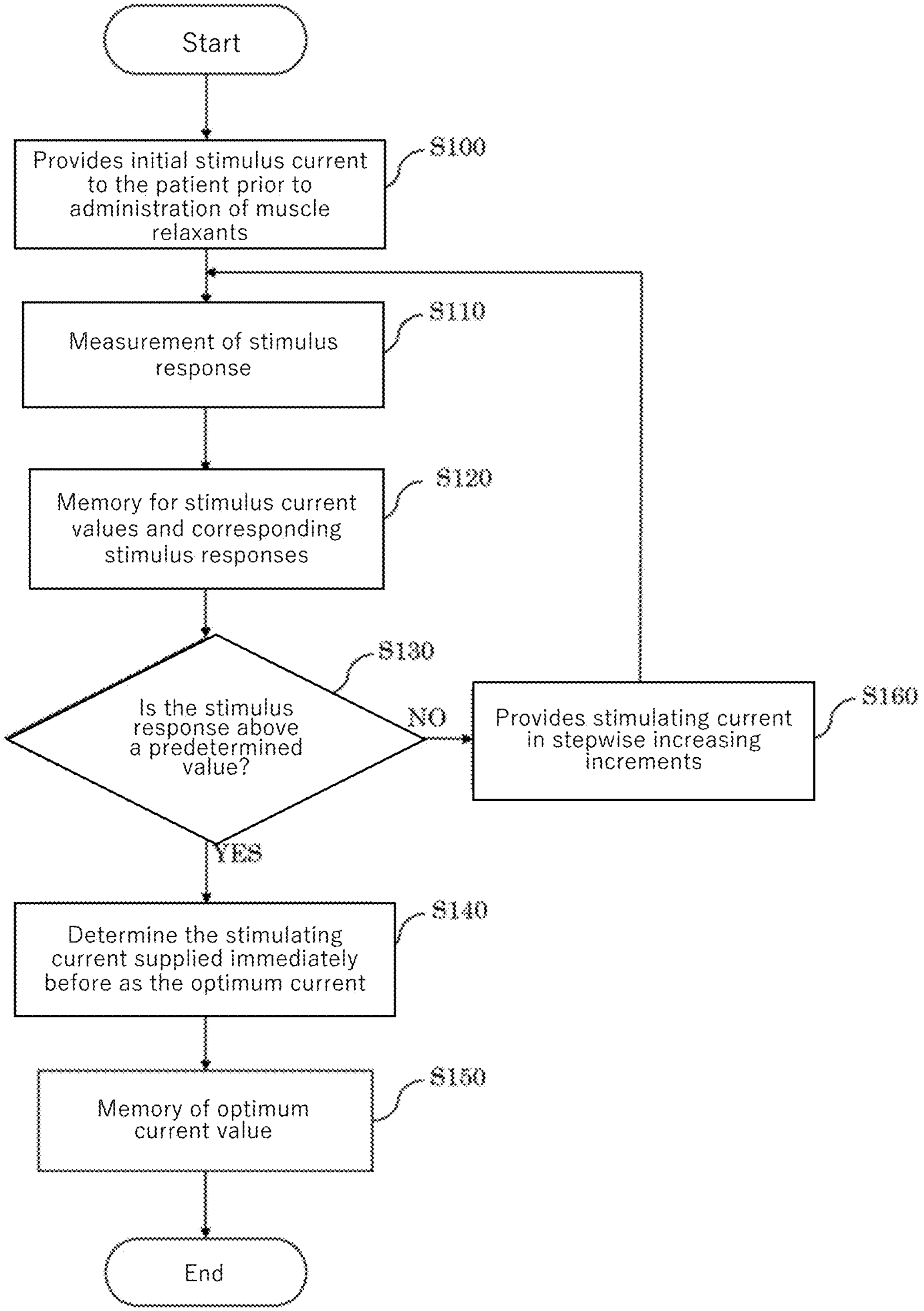

[Figure 4]
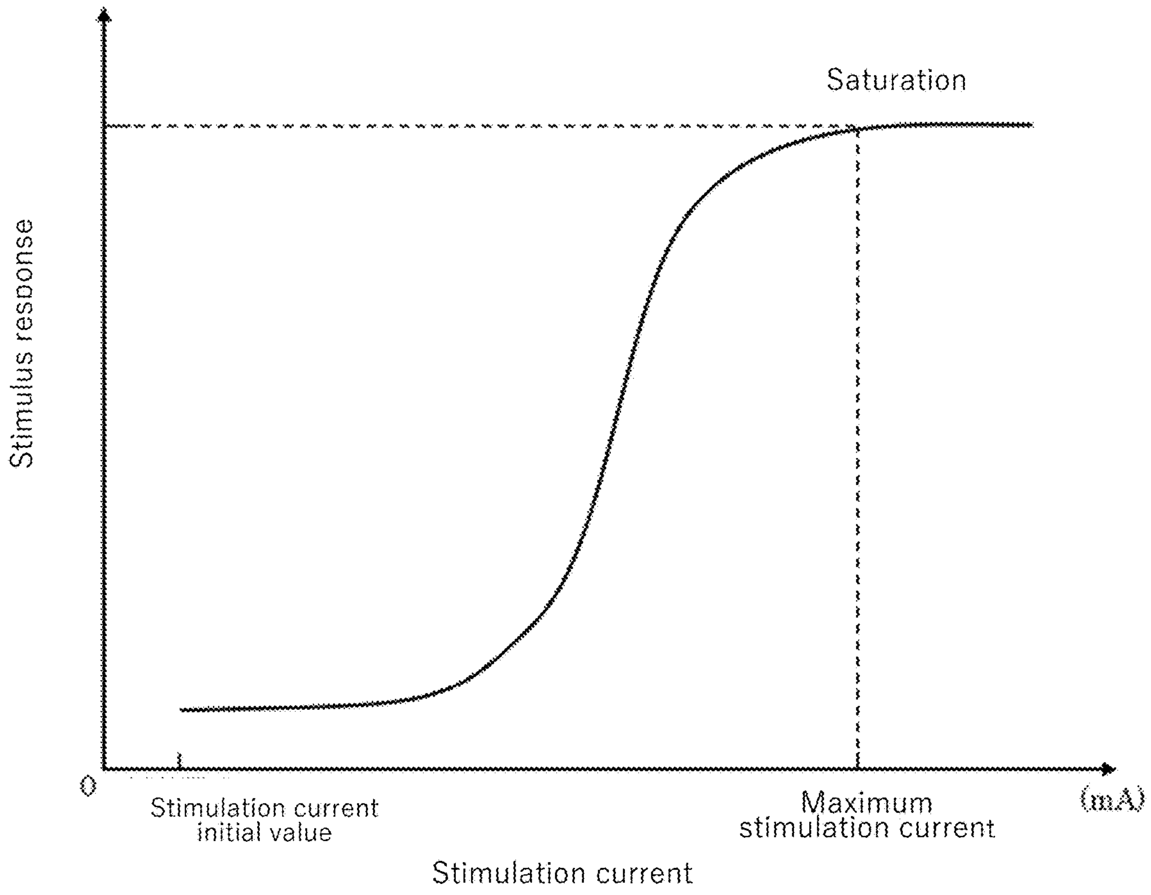

[Figure 5]
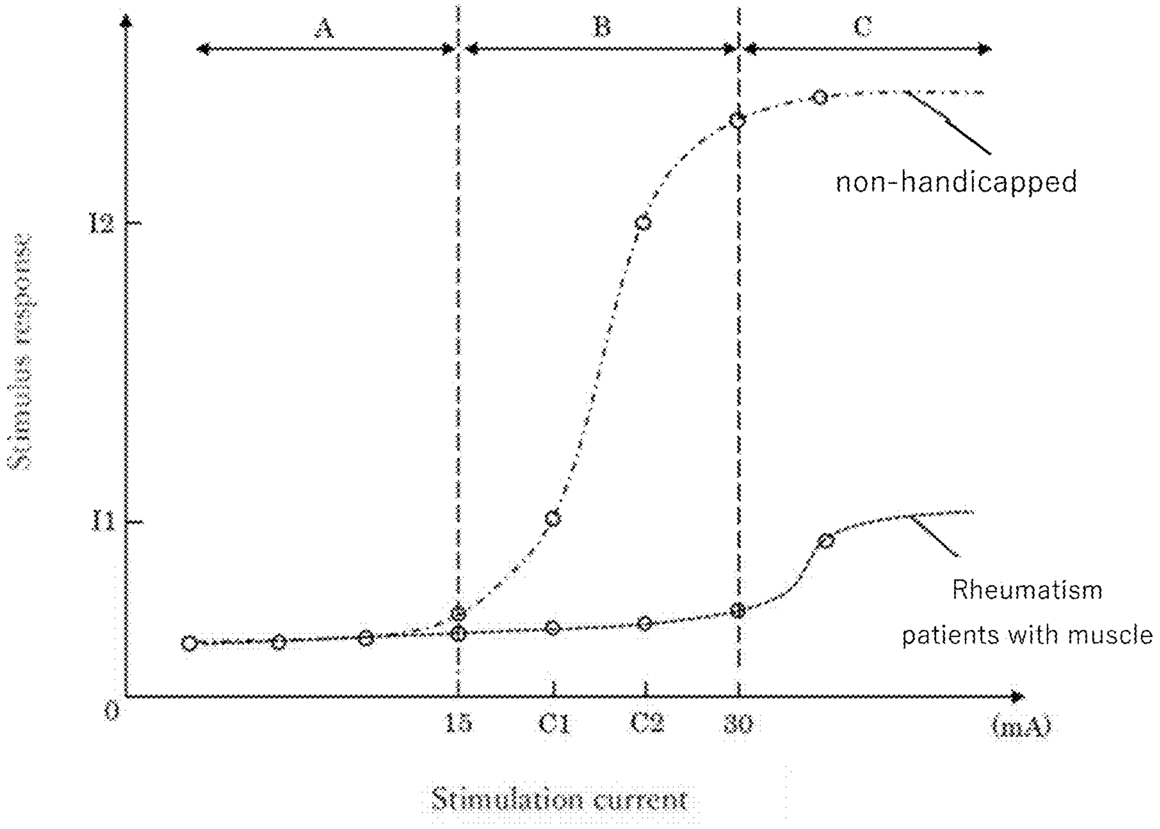

[Figure 6]
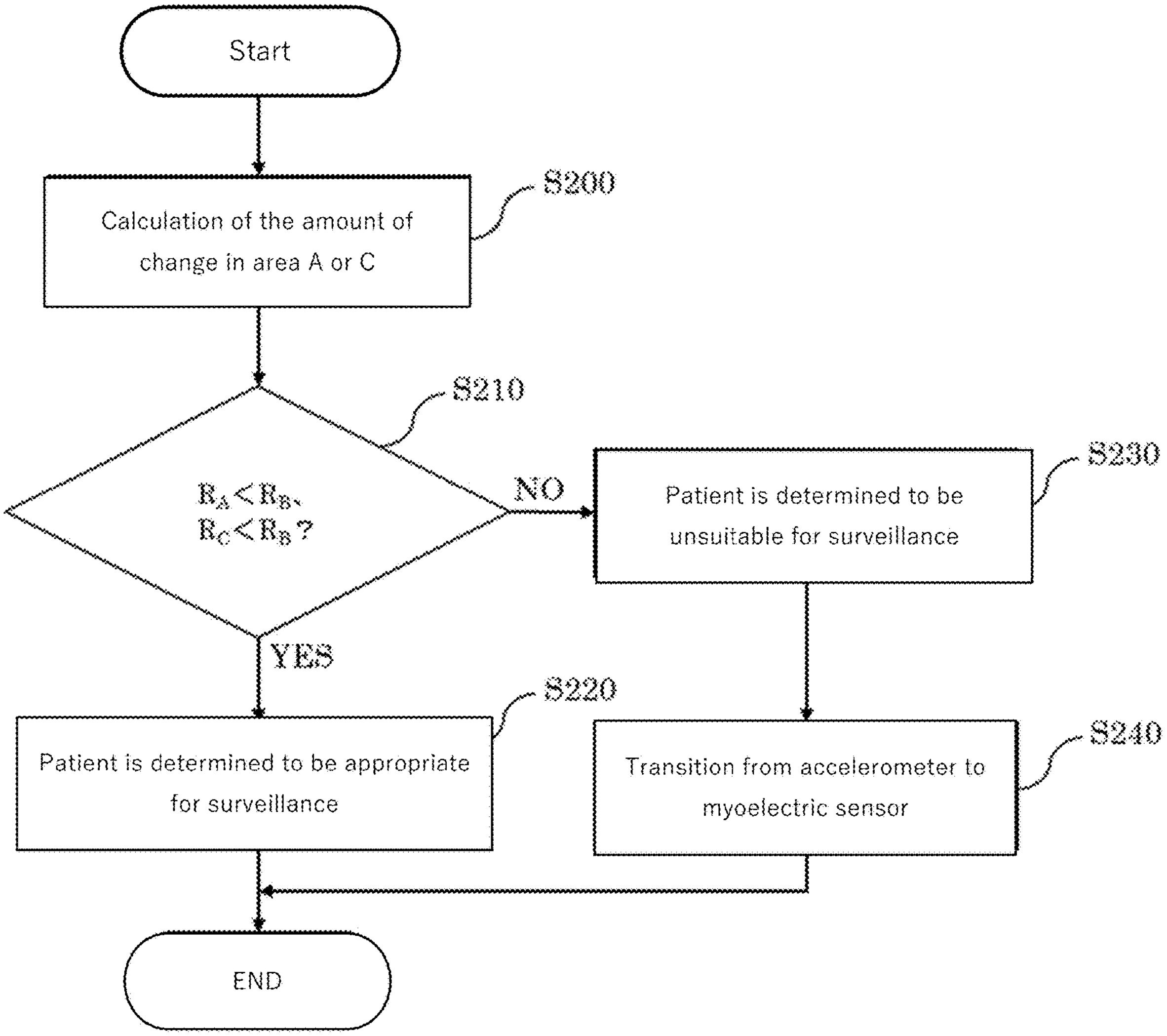

[Figure 7]
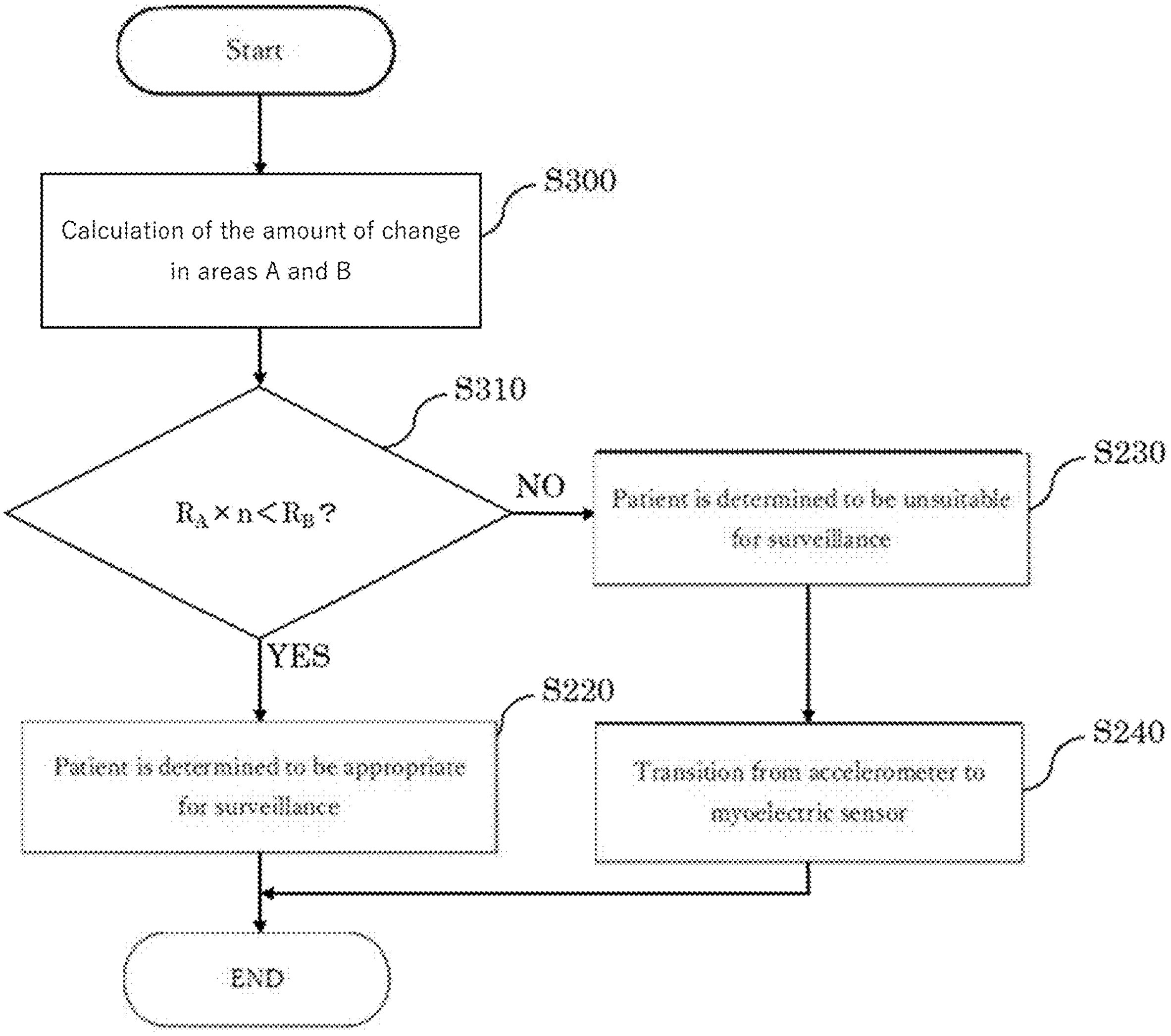

MUSCULAR RELAXATION MONITORING DEVICE

CROSS REFERENCE TO RELATED APPLICATIONS

This application is a U.S. National Stage Application, which claims the benefit under 35 U.S.C. § 371 of International Patent Application No. PCT/JP2022/014069 filed Mar. 24, 2022, which claims the foreign priority benefit under 35 U.S.C. § 119 of Japanese Patent Application No. 2021-064510 filed Apr. 6, 2021 the contents of which are incorporated herein by reference.

BACKGROUND

The inventors believe that a muscle relaxation monitoring device should be capable of monitoring the state of muscle relaxation without placing an excessive burden on the patient.

Sufficient relaxation of a patient's muscles is an indispensable condition for general anesthesia. The methods to relax muscles include inhibition of central nerves, blockade of peripheral nerves, blockade of neuromuscular junctions, and inhibition of the muscles themselves. Muscle relaxants are designed to relax skeletal muscles reversibly by blocking neuromuscular junctions.

It is also important to determine the patient's muscle relaxation state during and after surgery. In particular, accurate monitoring and detection of the disappearance of residual relaxation due to muscle relaxants and neuromuscular recovery after surgery is a factor in determining the dosage of antagonist drugs, as well as an indicator for removing the ventilator that was intubated into the patient.

Another method of detecting neuromuscular recovery is to determine it from the patient's grip strength based on the physician's hand sensation, but this is not quantitative or objective, and there is concern that it may increase the burden on the patient.

Therefore, various detection devices have been developed to quantitatively and objectively evaluate neuromuscular recovery (e.g., Japanese Patent Publication No. 2017-113085 or Japanese Patent Publication No. H10-57320).

In conventional devices, an electrical stimulus of about 50 mA is applied to the patient's hand to cause involuntary contraction of the patient's muscles, and the degree of movement is measured by an acceleration sensor. The measured stimulus response is used to determine the disappearance of residual relaxation and the neuromuscular recovery status.

SUMMARY

However, there are individual differences in muscle response to stimulation, and the conventional method of providing the same electrical stimulation to all patients may result in excessive stimulation for the patient. In other words, some patients may feel pain from the electrical stimulation after awakening.

The inventors propose to provide a muscle relaxation monitoring device that can monitor the state of muscle relaxation without placing an excessive burden on the patient.

The proposed muscle relaxation monitoring device is equipped with current stimulator for supplying a stimulating current to a patient's muscle, reaction detector for detecting the stimulation response of the muscle stimulated by the current stimulator. A stimulating current to the patient's muscles before the application of muscle relaxants, with a stepwise increase in the amount of the stimulating current supplied and a memory for recording the stimulating current supplied to the patient's muscle in a stepwise increasing manner and the stimulation response corresponding to the stimulating current value before the muscle relaxant is applied. Furthermore, the system is equipped with a controller that determines the stimulation current value immediately before saturation as the optimum current value to be supplied to the patient after administration of the muscle relaxant when the stimulation response is saturated.

Thus, according to the proposal, the stimulating current supplied to the patient's muscle in a stepwise increasing manner and the stimulating response corresponding to the stimulating current value are recorded in the memory before the muscle relaxant is applied. The controller determines the stimulation current value immediately before saturation as the optimum current value to be supplied to the patient after administration of the muscle relaxant. Thus, the stimulation current to be supplied can be determined according to the individual patient, and the optimum current value is the stimulation current value immediately before saturation at which the patient's burden to electrical stimulation is small and the muscle relaxation state can be accurately detected. This has the effect of enabling accurate monitoring of the muscle relaxation state without placing an excessive burden on the patient.

In the muscle relaxation monitoring device, the reaction detector is an electromyogram sensor and an acceleration sensor, if necessary.

In this way, the proposal utilizes myoelectric sensors and acceleration sensors as reaction detector, thus eliminating the need for a fixing stand to fix the arm or hand tip, which is necessary when the strength of the force applied from the thumb is detected by a strain gauge. Therefore, the effect is that the device can be downsized.

In the proposed muscle relaxation monitoring device, the controller, if necessary, calculates the amount of change in the stimulus response to the stimulus current before the muscle relaxant input near the initial supply, near saturation, and in between, respectively, with respect to the stimulus current, and determines whether the patient is an appropriate subject for monitoring based on the amount of change.

Thus, whether a patient is appropriate for monitoring or not is determined based on the amount of change in stimulus response to the stimulus current. Thus, it is possible to distinguish between patients suffering from diseases of the muscles, joints, or nervous system, who draw different stimulus-current-stimulus-response curves, and patients who do not suffer from these diseases (healthy subjects). As a result, the effect is that only healthy subjects suitable for monitoring with the device can be selectively monitored.

The muscle relaxation monitoring device determines, if necessary, to shift from accelerometer to electromyography as a reaction detection method when the controller determines that the patient is inappropriate as a monitoring target.

Thus, the controller decides to shift to the myoelectric sensor as a reaction detector when the patient is judged to be inappropriate as a monitoring target, not due to a disease originating from the patient, but due to a failure of the accelerometer or the like, and the acceleration of the muscle This has the effect of encouraging monitoring of the myorelaxation state with the electromyography sensor, which is not based on changes in muscle acceleration, thereby enabling the patient's myorelaxation state to be grasped more reliably.

BRIEF DESCRIPTION OF THE DRAWINGS

These and/or the other aspects and advantages will become apparent and more readily appreciated from the following description of the embodiments, taken in conjunction with the accompanying drawings.

FIG. 1 is a schematic diagram of the muscle relaxation monitoring device of the first embodiment.

FIG. 2 is a block diagram of the main unit of the muscle relaxation monitoring device of the first embodiment.

FIG. 3 is a flowchart showing the operation of the determination of the optimum current value in the muscle relaxation monitoring device of the first embodiment.

FIG. 4 is a graph showing changes in the stimulus response of a healthy subject to a stimulus current.

FIG. 5 is a graph showing the change in stimulus response to the stimulus current of a healthy subject measured by the muscle relaxation monitoring device of the second embodiment.

FIG. 6 is a flowchart showing the operation of the judgment process for determining suitability as a monitoring target in the muscle relaxation monitoring device of the second embodiment.

FIG. 7 is a flowchart showing another example of the operation of the determination of suitability as a monitoring target in the muscle relaxation monitoring device according to the second embodiment.

DETAILED DESCRIPTION OF THE PREFERRED EMBODIMENTS

The following is a description of at least one embodiment of the inventors' proposals. The same symbols are used for the same elements throughout this form.

The first embodiment of the muscle relaxation monitoring device is described using FIGS. 1 through 3. FIG. 1 shows a schematic diagram of the muscle relaxation monitoring device of this embodiment, FIG. 2 shows a block diagram of the main unit of the muscle relaxation monitoring device, and FIG. 3 shows a schematic diagram of the operation of determining the optimal current value in the muscle relaxation monitoring device of this embodiment. FIG. 3 is a flowchart showing the operation of the determination of the optimum current value in the device.

As shown in FIG. 1, the muscle relaxation monitoring device 1 has a main unit 10 that is fixed and supported on the forearm portion of the patient 100 via a band 50 or the like. It also has electrode clips 20 and 21 corresponding to current stimulators, which are attached near the ulnar nerve of the forearm of patient 100 and supply a stimulating current to the ulnar nerve via wiring 40 and 41. It also has an electromyography sensor 30 corresponding to the response detection portion, which is attached to the distal phalanx and the ball of the thumb, which is near the adductor internus muscle of the thumb of patient 100, via wiring 42, and measures muscle potentials. It has an accelerometer 31 corresponding to the reaction detection part, which is attached to the thumb terminal segment of the patient 100 in an integral configuration with the myoelectric sensor 30 and measures the acceleration changes of the muscle. The muscle relaxation monitoring device 1 is connected wirelessly or wired to a medical telemeter or other device not shown in the figure.

The main unit 10 is equipped with an operation button 10*a* as a control unit into which various instructions from medical personnel are input, and a display The display 10*b* is equipped with an LCD (Liquid Crystal Display). The display 10*b* is an LCD (Liquid Crystal Display), OLED (Organic EL ElectroLuminescence) or other color or monochrome displays.

The operation buttons 10*a* and the display 10*b* may be integrally configured as a so-called touch panel.

Electrode clips 20 and 21 are attached via electrode pads 22 and 23 to the patient 100 on the forearm (wrist side), which is in the vicinity of the ulnar nerve of the hand. To ensure secure attachment to the patient 100, the surfaces of the electrode pads 22 and 23 may be coated with an adhesive. The electrode pads 22 and 23 may be coated with an adhesive to ensure that they are attached to the patient 100.

The myoelectric sensor 30 has electrode pads 30*a* and 30*b*, which are attached to the distal phalanx and the ball of the thumb, which are in the vicinity of the adductor internus muscle of the thumb, and a ground electrode 30*c*. The sensor 30 is composed of electrode pads 30*a* and 30*b*, which are attached to the thumb distal phalanx and thumb ball, and a ground electrode 30*c*.

Accelerometer 31 is attached to the terminal phalanx of the thumb of patient 100, integrally configured with the electrode pad 30*a* of the myoelectric sensor 30.

For example, a 3-axis acceleration sensor can be used as the acceleration sensor 31, although this is not particularly restricted. When a 3-axis acceleration sensor is used as acceleration sensor 31, the sum of the 3 orthogonal direction vectors of the 3D sensor is detected as the amount of motion.

Thus, since acceleration sensor 31 (or myoelectric sensor 30) is used as the reaction detection part, a fixed tool or the like to fix the arm or the tip of the hand becomes unnecessary. This eliminates the need for a fixed stand to secure the arm or fingertip, which would be necessary if a strain gauge were used to detect the strength of the force applied by the mother finger. Therefore, the device can be downsized.

The combination of electrode clips 20 and 21 and the attachment positions of myoelectric sensor 30 and accelerometer 31 can be a combination of ulnar nerve/maternal adductor muscle as well as ulnar nerve/femoral adductor muscle, ulnar nerve/first dorsal interosseous muscle, posterior tibial nerve/short phalanges flexor muscle, facial nerve/orbicularis oculi muscle, and facial nerve/wrinkle eyebrow muscle. This combination would avoid direct stimulation of the muscle and attach to neuromuscular sites where single contractions can be more clearly detected.

Wires 40 to 42 are converged as a wiring bundle in an insulated state, compacted and connected to the main unit 10. The wiring bundles are connected to the main unit 10 in an insulated state.

The stimulating electrodes (corresponding to electrode pads 22 and 23), myoelectric sensor 30 and acceleration sensor 31 may be configured to be connected to the main unit 10 wirelessly. It is also possible to configure all of the stimulating electrodes, as well as the myoelectric sensor 30 and the acceleration sensor 31, as an integral part of the main unit 10.

Next, the internal configuration of the main unit 10 of the muscle relaxation monitoring device 1 will be described.

As shown in FIG. 2, the muscle relaxation monitoring device 1 has a current stimulating unit 11 that supplies a stimulating current to the muscles of patient 100 and a reaction detecting unit 12 that detects the stimulation response of the muscles stimulated by the current stimulating unit 11. The current stimulator 11 generates a stimulating current that is supplied to the muscles of the patient 100 in a stepwise increasing manner before the muscle relaxant is applied, and has a memory unit 13 that records the stimulating response corresponding to the stimulating current value. The muscle relaxation monitoring device 1 has a control unit 14 that determines the stimulation current value immediately before saturation as the optimum current value to be supplied to the patient 100 after administration of the muscle relaxant when the stimulation response is saturated.

The muscle relaxation monitoring device 1 is further equipped with a control unit 15, a display unit 16, and an input/output unit 17.

The current stimulators 11 corresponding to the electrode clips 20 and 21 are used to stimulate the muscles of the patient 100 in accordance with the control unit 14 Based on the commands, a predetermined stimulating current (details to be described later) is supplied to the muscles of patient 100 in a predetermined stimulation pattern.

The stimulation pattern is a single contraction stimulation pattern.

The stimulation patterns include single contraction stimulation, TOF (Train Of Four) stimulation, and double burst stimulation. Of Four (TOF) stimulation, double burst stimulation, tetanus stimulation, post-tetanic count (PTC) stimulation, etc. PTC, etc. can be selected as appropriate.

Of these, TOF stimulation, for example, is a set of four consecutive stimulations every 0.5 seconds, which are repeated to stimulate the target nerve. In this case, the stimulation frequency is 2 times/second, which corresponds to 2 Hz. The interval between each set is set at an appropriate time interval (e.g., 10 to 20 seconds) to allow the nerve to regenerate its responsiveness to stimulation.

Response detection unit 12, corresponding to myoelectric sensor 30 and accelerometer 31, detects the stimulus response of the muscle stimulated by current stimulator 11. For example, when TOF stimulation is selected as the stimulation pattern in the current stimulation section 11, the stimulation response (stimulation intensity) from the first muscle contraction (T1) to the fourth muscle contraction (T4) is detected as electrical signals from myoelectric sensor 30 and accelerometer 31 located on the thumb terminal segment of patient 100. The electrical signals from the myoelectric sensor 30 are amplified by an amplifier, not shown, to transmit the stimulus response to the response detection unit 12.

The response detection unit 12 transmits the detected T1 to T4 stimulus responses to the control unit 14.

The control unit 14 is equipped with a central processing unit (CPU) that controls various aspects of the muscle relaxation monitoring device 1, various programs that the CPU executes to control the muscle relaxation monitoring device 1, and internal memory in which various data are stored.

The control unit 14 reads data and programs stored in the internal memory and performs various arithmetic operations to realize various functions.

The control unit 14 stores the stimulation current values supplied to the muscles of the patient 100 via the current stimulation unit 11 in the memory unit 13. The control unit 14 stores the stimulus response corresponding to the stimulus current value transmitted from the response detection unit 12 in the memory unit 13. As described below, the stimulation current value just before the stimulation response is saturated in the measurement data stored in the memory section 13 is determined as the optimum current value to be supplied to the patient 100 after administration of the muscle relaxant.

The control panel 15 corresponding to the control button 10*a* is an interface for making various inputs to the muscle relaxation monitoring device 1.

The display 16 corresponding to the display 10*b* shows the execution program that the muscle relaxation monitoring device 1 is performing on the patient 100, the stimulation current value and stimulation pattern being supplied to the patient 100, and the stimulation response detected by the myoelectric sensor 30 and the acceleration sensor 31.

The input/output section 17 transmits and receives data to and from the medical telemeter via radio or cable lines. The input/output section 17 has an antenna and electrical connectors. For example, the input/output section 17 transmits the stimulation current value supplied to the patient 100 and the stimulation response detected by the response detection section 12 to the medical telemeter.

Next, the processing operation for determining the optimum current value in the muscle relaxation monitoring device 1 will be described. Although either myoelectric sensor 30 or acceleration sensor 31 may be used as the sensor corresponding to the reaction detection section 12, the following explanation is based on the case where acceleration sensor 31 is used.

First, a medical care worker operates the operation button 10*a* on the main unit 10 of the muscle relaxation monitoring device 1 attached to the patient 100 before administering a muscle relaxant. The operation unit 15 sends an input signal to the control unit 14. The control unit 14 then sends an instruction to the current stimulator 11 to supply the patient 100 with the initial value of stimulation current in the prescribed stimulation pattern (step S100). 1 to transmit an instruction to the current stimulator 11 (step S100).

Specifically, for example, nerve stimulation is performed on patient 100 with TOF stimulation as the stimulation pattern and 10 mA as the initial stimulation current.

Next, when the reaction detection unit 12 receives an electrical signal (stimulus response) from the acceleration sensor 31 due to contraction of the muscles of the patient 100, it transmits said stimulus response to the control unit 14 (step S110). The control unit 14 temporarily stores the stimulus current value transmitted to the current stimulator 11 and the stimulus response in response to said stimulus current value in the memory unit 13 at least until the processing operation to determine the optimum current value is completed (step S120).

Specifically, for example, when TOF stimulation is selected as the stimulation pattern, the stimulation response at the first muscle contraction (T1) is stored. The control unit 14 stores the stimulus response in the memory unit 13 as the stimulus response corresponding to the current value.

Next, the control unit 14 determines whether the stimulus response transmitted from the response detection unit 12 exceeds the predetermined value set in advance (step S130).

The predetermined value of the stimulus response is the value when the stimulus response is saturated in response to the supplied stimulus current. As shown in FIG. 4, it is known that the stimulus response to the stimulus current saturates (does not change) at a certain value for any given stimulus current (different for each patient), regardless of whether the myoelectric sensor 30 or the accelerometer 31 is used. In this embodiment, this saturated stimulus response is used as the predetermined value of the stimulus response.

If the stimulus response does not exceed the predetermined value (step S130: NO), the control unit 14 sets a new stimulus current value (step S160) by increasing the initial stimulus current value in steps, and repeats steps S110 through S130 and step S160 until the stimulus response exceeds the predetermined value. Steps S110 through S130 and S160 are repeated until the stimulus response exceeds the predetermined value.

Specifically, for example, one second after supplying the initial stimulation current value to patient 100, a stimulation current with a 5 mA increase from the initial stimulation current value of 10 For example, one second after the initial value of the stimulation current is supplied to patient 100, the stimulation current is increased by 5 mA from the initial value of the stimulation current of 10 mA to stimulate the nerves. The nerve stimulation is repeated while increasing the stimulation current by 5 mA in steps of 5 mA at 1 second intervals until the stimulation response exceeds a predetermined value.

When the stimulus response exceeds the predetermined value (step S130: YES), the control unit 14 stops supplying the stimulus current to the patient 100. Next, the control unit 14 determines the stimulation current value stored in the memory section 13 immediately before the stimulation response exceeds the predetermined value as the optimum current value (step S140). Next, said optimum current value is stored in the memory section 13 (step S150). Then, the operation of determining the optimum current value is terminated.

Specifically, suppose, for example, that the stimulus response exceeds a predetermined value at a stimulus current of 45 mA. In this case, the stimulation current value of 40 mA, which is the stimulation current value immediately before that point, is determined and stored as the optimal current value.

The optimum current value thus determined is displayed on the display 10*b*.

The control unit 14 may transmit the determined optimum current value to the medical telemeter via the input/output unit 17, and the medical telemeter may store and display the value in connection with patient information.

After the administration of the muscle relaxant (during and after surgery), the optimal current value determined as described above is used to determine the muscle relaxation and recovery state of the patient 100 at the acceleration sensor 31.

In this case, the control unit 14 may perform the normalization process (normalization) prior to surgery (prior to muscle relaxant administration). For example, when TOF stimulation is used as the stimulation pattern, the ratio of the first muscle contraction (T1) to the stimulation response of the first muscle contraction (T2) If the ratio of the stimulus response of the fourth muscle contraction (T4) to the stimulus response of the first muscle contraction (T1) (TOF ratio:T4/(TOF ratio:T4/T1) sometimes exceeds 1. This is because the joints become accustomed to the stimulating current and the joint movements become smooth, and the fourth stimulus response (stimulus intensity) is greater than the first stimulus response (stimulus intensity).

Therefore, during the monitoring phase by the device before the surgery of patient 100, a normalization process is performed to set the TOF ratio:T4/T1 to 1. Specifically, if T4/T1=1.2 before the surgery, this value is normalized to 1. In this example, all TOF ratios are thereafter processed as T4/T1×1/1.2.

For example, when the muscle relaxation state and recovery state of patient 100 is determined using TOF stimulation as the stimulation pattern, control unit 14 first retrieves the optimum current value for patient 100 from memory unit 13 and commands current stimulation unit 11 to supply stimulation current to patient 100 at said optimum current value.

The current stimulation unit 11 nerve-stimulates patient 100 via electrode clips 20 and 21, and the response detection unit 12 receives the contraction of the muscles of patient 100 in response to said nerve stimulation as an electrical signal from the accelerometer 31.

Next, the control unit 14 calculates the ratio (TOF ratio: T4/T1) of the stimulus response of the fourth muscle contraction (T4) to the stimulus response of the first muscle contraction (T1) based on the stimulus response transmitted from the response detection unit 12.

Since the stimulus response gradually decreases from the first to the fourth stimulus, the recovery state of patient 100 can be easily ascertained by observing the TOF ratio.

For example, if this TOF ratio meets the condition that T4/T1>0.9 (after normalization process), the control unit 14 determines that the patient 100 is in a state of recovery and displays this on the medical telemeter via the display 10*b* and input/output unit 17.

In response, the medical personnel removes the ventilator intubated in patient 100, etc., and the monitoring of the muscle relaxation state of patient 100 is completed.

As described above, the stimulation current supplied to the muscles of patient 100 before the muscle relaxant is applied and the stimulation response corresponding to the stimulation current value are recorded in memory section 13, and control section 14 determines the stimulation current value immediately before saturation as the optimal current value to be supplied to patient 100 after the muscle relaxant is applied. Thus, the stimulation current to be supplied can be determined according to the individual patient. This allows the optimal current value to be the stimulation current value just before saturation, where the patient's burden for electrical stimulation is small and the muscle relaxation state can be accurately detected. The muscle relaxation state can be accurately monitored without placing an excessive burden on the patient 100.

The muscle relaxation monitoring device of the second embodiment is described using FIGS. 5 through 7. FIG. 5 is a graph showing changes in the stimulus response of healthy subjects, etc. to the stimulus current measured by the muscle relaxation monitoring device of this embodiment, and FIG. 6 is a flowchart showing the processing operation for judging the suitability as a monitoring target in the muscle relaxation monitoring device of this embodiment. FIG. 7 is a flowchart showing another example of the processing operation for judging the suitability of a subject for monitoring in the muscle relaxation monitoring device of this embodiment.

In this embodiment, explanations that overlap with the first embodiment above are omitted.

The control unit 14 calculates, for the patient 100 before the administration of the muscle relaxant, the amount of change in the stimulus response to the stimulus current before the muscle relaxant input in the vicinity of the initial supply, the vicinity of saturation, and in the middle thereof, with respect to the stimulus current. The control unit 14 calculates the amount of change in the stimulus response to the stimulus current for the patient 100 before the administration of the muscle relaxant, and determines whether or not the patient is an appropriate target for monitoring based on the amount of change.

Patients with joint or muscle abnormalities, such as rheumatoid patients or patients with muscle atrophy (e.g., dialysis patients), show different stimulus responses from patients without such abnormalities (hereinafter referred to as "normal" patients).

As shown in FIG. 5, when patient 100 is a healthy subject, a slight stimulus response is observed in region A, which is the beginning of the stimulus current supply, followed by a rapid rise in the stimulus response in region B. In area B, the stimulus response rises rapidly, and in area C, the stimulus response to the stimulus current is saturated and almost no change in the stimulus response is observed. In the present study, the range of the stimulation current is 15 to 30 mA for region B. However, this is not limited to the range of 15 to 30 mA. It can be set appropriately based on the stimulation current-stimulus response curve of a healthy subject.

In other words, the change in stimulus response RA or RC in relation to the stimulus current value in each region of a healthy subject shows the following relationship.

$$RA<RB, RC<RB$$

Here, the amount of change in the stimulus response to the stimulus current in each region is calculated from any two measurements data, continuous or discontinuous, among multiple data including data on the boundaries with adjacent regions.

For example, in the example shown in FIG. 5, the amount of change in stimulus response to the stimulus current of a healthy subject in region B, RB, is;

$$RB=(I2-I1)/(C2-C1)$$

When selecting any two measurements data, it is preferable to select data with a large difference between the stimulated current value C1 and the stimulated current value C2 in each region, since the characteristics of the approximate curves in each region are more significant. This is preferable because it represents the characteristics of the approximate curve in each region.

In addition, in each region, the amount of change for two consecutive measurement data may all be calculated, and the average of these may be used as the (average) amount of change in the stimulus response to the stimulus current.

In contrast, patients with rheumatoid arthritis and myasthenia show almost no rise in stimulus response in the regions corresponding to regions A and B of the curve showing normal subjects, and a slight stimulus response is observed in the region corresponding to region C. The patients with rheumatoid arthritis and atrophied muscles showed a slight increase in the stimulus response in the area corresponding to area C.

In other words, the change in stimulus response to the stimulus current in each region of the curve for patients with rheumatoid arthritis and myasthenia shows the following relationship: RA and RC are the change in stimulus response to the stimulus current in each region.

$$RA<RC, RB<RC$$

As described above, the stimulus response to the stimulus current is different between healthy subjects and rheumatoid/myoclonic patients, and sufficient stimulus response cannot be observed. This means that rheumatoid arthritis/myoclonus patients are inappropriate as targets for monitoring the muscle relaxation state using the accelerometer.

Therefore, the muscle relaxation monitoring device 1 determines whether the patient 100 is appropriate for monitoring based on the amount of change in the stimulus response to the stimulus current.

The following is an explanation of the processing operation for determining suitability as a monitoring target in this embodiment of the muscle relaxation monitoring device 1. This suitability determination processing operation is performed in parallel with, but not limited to, the optimal current value determination processing operation described in the first embodiment above.

First, the control unit 14 determines, from the stimulation current value transmitted to the current stimulator 11 and the corresponding stimulation response received from the response detection unit 12, the optimum current value for the stimulation area A and C. First, the control unit 14 calculates the amount of change in the stimulus response to the stimulus current in the preset areas A to C as needed (step S200).

For example, the following values are set as the stimulation current values for regions A through C.

Area A: 10 to 15 mA, Area B: 15 to 30 mA, and Area C: 30 mA or the maximum stimulation current value.

As a result, if the calculated change satisfies RA<RB and RC<RB (Step S210: YES), then patient 100 is a healthy person, it is determined (step S220) that the patient is appropriate to be monitored by the muscle relaxation monitoring device 1, and this is indicated on the display 10*b*, medical telemeter, etc. The suitability judgment processing operation is completed by displaying this fact on the display 10B, medical telemeter, etc.

If patient 100 is determined to be appropriate as a monitoring target, even after the administration of the muscle relaxant, the optimal current value determined in the optimal current value determination processing operation is used to determine the optimal current value, and the acceleration sensor 31 to monitor the muscle relaxation and recovery status of patient 100.

If the calculated change does not satisfy RA<RB and RC<RB (step S210: NO), it is determined (step S230) that patient 100 is inappropriate to be monitored by the muscle relaxation monitoring device 1. (step S230), and this is indicated on the display 110*b*, medical telemeter, etc. 0b, a medical telemeter, or the like. At this time, the medical personnel may be notified of the inappropriateness by a warning sound or other means.

If patient 100 is determined to be inappropriate as a monitoring target, the patient 100's muscle relaxation state may be determined based on the rule of thumb by the medical professional or the conventionally adopted default stimulation current (e.g., the same stimulation current value for all patients). The muscle relaxation state of patient 100 is to be ascertained.

Apart from the disease of patient 100, another reason why patient 100 is determined to be inappropriate for monitoring is that accurate data cannot be obtained due to a malfunction of the accelerometer 31 or other reasons. In addition, the movement of the thumb may be restricted by rubbing against the bed sheet during surgery or by external stresses. In addition, the 31 accelerometers may respond to motion in areas other than the thumb (body movement).

Therefore, in the suitability determination processing operation, the control unit 14 determines the optimal current value for the patient 100 before administering the myorelaxant as a way to determine the optimal current value for the patient 100, and the acceleration sensor 31 to myoelectric sensor 30 (step S240) as a way to determine the optimal current value for patient 100 prior to administration of the muscle relaxant, and this is The system may be configured to inform the medical personnel by a warning tone or other means.

The suitability determination processing operation is completed as described above.

After the decision to shift to the myoelectric sensor 30, the control unit 14 switches from the accelerometer 31 to the myoelectric sensor 30 as the reaction detection unit 12 as the medium for detecting the stimulus response of the patient 100, and performs the processing operation for determining the optimal current value and the suitability judgment processing operation (excluding the decision to shift to the myoelectric sensor) using the myoelectric sensor 30 The patient is then switched to the myoelectric sensor 30 from the acceleration sensor 31.

If patient 100 is determined to be appropriate for monitoring in the suitability/failure judgment processing operation (i.e., if there is a failure or other cause in acceleration sensor 31), after administration of the muscle relaxant, the muscle relaxation and recovery states of patient 100 are monitored using myoelectric sensor 30, using the optimal current value determined in the optimal current value determination processing operation. The state of the patient 100 is monitored. If patient 100 is determined to be inappropriate for monitoring, the muscle relaxation state of patient 100 is ascertained based on the rule of thumb by a medical professional or the default stimulation current conventionally employed.

In step S210, the judgment condition is whether or not both RA<RB and RC<RB are satisfied, but it is possible to judge whether or not patient 100 is appropriate for monitoring when the calculation of RB in area B is completed.

In other words, if patient 100 is a rheumatoid/myasthenic patient, the RB in region B does not exceed the threshold in relation to the RA in region A, since there is little difference in size between the RA in region A and the RB in region B, it can be determined that the patient is inappropriate for monitoring.

Specifically, for example, as shown in FIG. 7, after calculating the amount of change in the stimulus response to the stimulus current in regions A and B (step S300), if RA in region A and RB in region B satisfy RA×n<RB (step S310: YES), then patient 100 is determined to be an appropriate subject for monitoring in muscle relaxation monitoring device 1 (step S220). If RA×n<RB is not satisfied (step S310: NO), the patient 100 is determined to be inappropriate for monitoring in the muscle relaxation monitoring device 1 (step S230). Here, n is set appropriately from at least one or more values.

Thus, when the measurement of area B is completed, it is possible to determine whether or not patient 100 is appropriate as a monitoring target. If the processing operations for determining the optimum current value and the determination of suitability are performed in parallel, the subsequent processing operations for determining the optimum current value can be interrupted or stopped when the patient is determined to be unsuitable, and there is no need to supply extra stimulation current to the patient 100 who is determined to be unsuitable for monitoring. This eliminates the need to supply extra stimulating current to patients 100 who have been deemed inappropriate for monitoring, thereby reducing the burden on patient 100 with respect to the stimulating current.

The measurement data and/or the approximate curve derived from the measurement data may be displayed on the display 10*b* or medical telemeter. This allows the medical personnel to visually determine the suitability of the patient 100 as a target for monitoring.

As described above, since the determination of whether patient 100 is appropriate for monitoring is based on the amount of change in stimulus response to the stimulus current, it is possible to distinguish between patients suffering from diseases such as muscle and joint diseases (who draw different stimulus current-stimulus response curves) and those who do not suffer from these diseases (healthy subjects). The device is therefore suitable for monitoring with the device. Thus, the effect is that only healthy patients suitable for monitoring with the device can be selectively monitored.

The control unit 14 decides to shift to the myoelectric sensor 30 as the reaction detection unit 12 when the patient 100 is judged to be inappropriate as a monitoring target. Thus, when the patient 100 is judged to be inappropriate as a monitoring target not due to a disease originating from the patient 100 but due to a failure of the acceleration sensor 31, etc., the patient is encouraged to monitor the muscle relaxation state with the myoelectric sensor 30, which is not based on changes in muscle acceleration, and the effect is that the patient 100's muscle relaxation state can be grasped with greater certainty.

This section describes other embodiments of the muscle relaxation monitoring device.

The explanations that overlap with each of the above embodiments in this embodiment are omitted.

This embodiment of the muscle relaxation monitoring device 1 determines whether or not the acceleration sensor 31 is faulty after the muscle relaxation monitoring device 1 is started.

Accelerometer 31 may fail to output normal output values due to errors in output values caused by acceleration above the rated value due to falling or other causes, or by collisions during transportation. In such a state, the processing operations for determining the optimum current value and for judging the suitability of the sensor 31 will only cause unnecessary burden on the patient 100.

Therefore, in this embodiment, the failure judgment processing of acceleration sensor 31 is performed before the optimal current value determination processing operation or the suitability/failure judgment processing operation is performed.

First, after turning on the power of the muscle relaxation monitoring device 1, AC voltage is applied to excite the oscillator of the acceleration sensor 31, either automatically or by a healthcare professional selecting the diagnosis of a failure of the acceleration sensor 31 from the measurement menu.

Next, the control unit 14 receives the output signal from the acceleration sensor 31 due to the excitation of the transducer via the reaction detection unit 12, and if this output signal is If the output signal is greater than the threshold value, the acceleration sensor 31 is judged not to be faulty (good), and if the output signal is less than the threshold value, the acceleration sensor 31 is judged to be faulty (defective). and the failure determination process is terminated. The control unit 14 displays the judgment result on the display 10B and the medical telemeter, and also displays the acceleration sensor 3 If the control unit 14 determines that the acceleration sensor 31 is defective, it notifies the medical personnel by a warning sound or other means.

If the acceleration sensor 31 is determined to be faulty, the control unit 14 detects the reaction 12 as the acceleration sensor 31 to myoelectric sensor 30, and this may be reported to the medical personnel.

In each of the above embodiments, the processing operations for determining the optimum current value and for judging suitability are described using acceleration sensor 31 as the reaction detection unit 12 as an example, but myoelectric sensor 30 may also be used. In other words, instead of using the acceleration sensor 31, the myoelectric sensor 30 can be used as the reaction detection part 12, and the optimal current value determination processing operation and the appropriateness/inappropriateness judgment processing operation can also be performed using the myoelectric sensor 30. The decision to shift to the myoelectric sensor may be made by using the myoelectric sensor 30 as the reaction detection unit 12 without using the acceleration sensor 31.

During surgery, the control unit 14 may also perform a notification process to inform the medical personnel by control means a warning sound or other means that the TOF ratio has reached a predetermined value. For example, if the TOF ratio T4/T1 exceeds 0.25, body motion may be observed in the patient 100, which may interfere with the surgery. Therefore, one or more TOF ratios that may interfere with the surgery may be entered and set in advance in the muscle relaxation monitoring device 1 (internal memory, etc.), and when the TOF ratio measured during surgery reaches the set TOF ratio, the medical personnel may be notified by a warning sound or the like.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide* v. *DIRECTV*, 69 USPQ2d 1865 (Fed. Cir. 2004).

The invention claimed is:

1. A muscle relaxation monitoring device comprising: a current stimulator to supply a stimulating current to a muscle of a patient;

a stimulus response detector to detect a stimulus response of the muscle of the patient, that is produced by stimulating with the current stimulator;

a memory to record the stimulating current supplied to the muscle of the patient in steps increasing prior to administration of a muscle relaxant, and the stimulus response corresponding to each said stimulating current value;

and a controller to:

calculate an amount of change in the stimulus response to the stimulating current being increased from the initial supply current value, being increased to the saturation current value, and being increased in between the initial supply current value and the saturation current value, respectively, determine whether the patient is appropriate to be monitored based on the amount of change;

and identify when the stimulus response is saturated, and to determine an optimum current value, the optimum current value being the stimulating current supplied immediately before saturation, the controller setting the optimum current value as the current to be supplied to the patient after administration of the muscle relaxant.

2. The muscle relaxation monitoring device according to claim 1, wherein the stimulus response detector is at least one of an acceleration sensor and an electromyography sensor.

3. The muscle relaxation monitoring device according to claim 1, wherein the stimulus response detector comprises an acceleration sensor and an electromyography sensor.

4. A muscle relaxation monitoring device comprising:

a current stimulator to supply a stimulating current to a muscle of a patient;

a stimulus response detector to detect a stimulus response of the muscle of the patient, that is produced by stimulating with the current stimulator;

a memory to record the stimulating current supplied to the muscle of the patient in steps increasing prior to administration of a muscle relaxant, and the stimulus response corresponding to each said stimulating current value; and a controller to identify when the stimulus response is saturated, and to determine an optimum current value, the optimum current value being the stimulating current supplied immediately before saturation, the controller setting the optimum current value as the current to be supplied to the patient after administration of the muscle relaxant, wherein the stimulus response detector comprises an acceleration sensor and an electromyography sensor, and before the application of the muscle relaxant, the stimulating current is supplied to the muscle of the patient at an initial supply current value that is increased stepwise until at least a saturation current value, and the controller calculates an amount of change in the stimulus response to the stimulating current being increased from the initial supply current value, being increased to the saturation current value, and being increased in between the initial supply current value and the saturation current value, respectively, and the controller determines whether the patient is appropriate to be monitored based on the amount of change.

5. The muscle relaxation monitoring device according to claim 4, wherein the controller calculates the amount of change when the acceleration sensor is used as the stimulus response detector.

6. The muscle relaxation monitoring device according to claim 4, wherein when the controller determines that the patient is inappropriate as a monitoring target, it shifts from the acceleration sensor to the electromyography sensor as the stimulus response detector.

7. The muscle relaxation monitoring device according to claim 1, wherein after administration of the muscle relaxant to the patient, the controller monitors for any increase in the stimulus response to thereby monitor muscle relaxation.

8. The muscle relaxation monitoring device according to claim 7, wherein wherein if the controller identifies that the muscle of the patient is no longer relaxed after administration of the muscle relaxant, the controller outputs a signal to alert that the patient is in a state of recovery.

9. The muscle relaxation monitoring device according to claim 1, wherein the current stimulator comprises electrode clips.

10. A muscle relaxation monitoring device comprising: a current stimulator to supply a stimulating current to a muscle of a patient;

a stimulus response detector to detect a stimulus response of the muscle of the patient, that is produced by stimulating with stimulating current from the current stimulator; a memory to record the stimulating current supplied to the muscle of the patient, and the stimulus response corresponding to each stimulating current;

and a controller to:

increase the stimulating current stepwise prior to administration of a muscle relaxant to the patient;

calculate an amount of change in the stimulus response to the stimulating current being increased from the initial supply current value, being increased to the saturation current value, and being increased in between the initial supply current value and the saturation current value, respectively, determine whether the patient is appropriate to be monitored based on the amount of change;

identify saturation by determining when the stimulus response no longer increases stepwise despite the stimulating current being increased stepwise, and determine an optimum current value, the optimum current value being the stimulating current supplied immediately before saturation, the controller setting the optimum current value as the current to be supplied to the patient after administration of the muscle relaxant.

11. The muscle relaxation monitoring device according to claim 10, wherein the optimum current value produces an awake stimulus response before the muscle relaxant is administered to the patient, and the device further comprises a monitoring unit to monitor relaxation of the patient after administration of the muscle relaxant and to conclude that muscles are relaxed when the patient produces a stimulus response less than the awake stimulus response.

12. The muscle relaxation monitoring device according to claim 10, wherein the patient produces a baseline stimulus response when muscles are fully relaxed, and the control unit concludes that the muscles are in an active state when the patient produces a stimulus response greater than the baseline stimulus response.

13. The muscle relaxation monitoring device according to claim 10, wherein the stimulus response detector comprises an acceleration sensor and an electromyography sensor, and if, prior to administration of the muscle relaxant, the patient does not produce a stepwise increase in stimulus response using the acceleration sensor as the stimulus response detector, the controller switches from the acceleration sensor to the electromyography sensor as the stimulus response detector.

14. The muscle relaxation monitoring device according to claim 10, wherein the current stimulator comprises electrode clips.

* * * * *